United States Patent
Lu et al.

(10) Patent No.: US 9,506,804 B2
(45) Date of Patent: Nov. 29, 2016

(54) OPEN PATH GAS DETECTOR

(71) Applicant: Detector Electronics Corporation, Minneapolis, MN (US)

(72) Inventors: Liangju Lu, Eden Prarie, MN (US); John King, Roseville, MN (US)

(73) Assignee: DETECTOR ELECTRONICS CORPORATION, Minneapolis, MN (US)

( * ) Notice: Subject to any disclaimer, the term of this patent is extended or adjusted under 35 U.S.C. 154(b) by 0 days.

(21) Appl. No.: 14/760,608

(22) PCT Filed: Jan. 10, 2014

(86) PCT No.: PCT/US2014/011030
§ 371 (c)(1),
(2) Date: Jul. 13, 2015

(87) PCT Pub. No.: WO2014/113287
PCT Pub. Date: Jul. 24, 2014

(65) Prior Publication Data
US 2015/0355082 A1  Dec. 10, 2015

Related U.S. Application Data

(60) Provisional application No. 61/753,589, filed on Jan. 17, 2013.

(51) Int. Cl.
*G01N 21/00* (2006.01)
*G01J 3/36* (2006.01)
(Continued)

(52) U.S. Cl.
CPC .. *G01J 3/36* (2013.01); *G01J 3/42* (2013.01); *G01N 21/3504* (2013.01); *G01N 21/359* (2013.01); *G01N 21/39* (2013.01);
(Continued)

(58) Field of Classification Search
CPC .......... G02B 6/12007; G02B 6/12004; G02B 6/136; G02B 6/12019; G02B 6/12023; G02B 6/12033; G02B 6/131; G02B 6/4204; G02B 6/12011; G02B 6/12021; G02B 6/12026; G02B 6/12028; G02B 6/4214; G02B 6/4246
See application file for complete search history.

(56) References Cited

U.S. PATENT DOCUMENTS 4,264,209 A   4/1981  Brewster
5,202,570 A * 4/1993  Tanaka ................... G01N 21/39
                                                      250/205
(Continued)

FOREIGN PATENT DOCUMENTS

DE   4324118 A1   1/1995
WO   02082059 A1  10/2002

OTHER PUBLICATIONS

International Search Report for application PCT/US2014/011030, dated May 21, 2014, 5 pages.
(Continued)

*Primary Examiner* — Michael P Stafira
(74) *Attorney, Agent, or Firm* — Cantor Colburn LLP

(57) ABSTRACT

In implementations, an open path gas detector is disclosed that can include imaging or non-imaging optical components. The detector can include components that allow for misalignment of radiation received by the detector of about 1 without causing false alarms. In implementations, the detector can include a beam splitter or a wavelength-division multiplexing filter to allow for more of the radiation received by the detector to be detected by the sensors.

21 Claims, 13 Drawing Sheets

(51) Int. Cl.
- *G01J 3/42* (2006.01)
- *G01N 33/00* (2006.01)
- *G01N 21/359* (2014.01)
- *G01N 21/39* (2006.01)
- *G01N 21/3504* (2014.01)
- *G01J 3/28* (2006.01)

(52) U.S. Cl.
CPC ......... *G01N33/0031* (2013.01); *G01J 3/2823* (2013.01); *G01J 2003/423* (2013.01); *G01N 2021/3513* (2013.01)

(56) References Cited

U.S. PATENT DOCUMENTS

| | | |
|---|---|---|
| 5,401,967 A | 3/1995 | Stedman et al. |
| 5,693,944 A | 12/1997 | Rich |
| 5,767,976 A | 6/1998 | Ankerhold et al. |
| 6,061,141 A | 5/2000 | Goldenberg et al. |
| 6,191,421 B1 | 2/2001 | Yamamori et al. |
| 6,194,735 B1 | 2/2001 | Martin |
| 6,455,854 B1 | 9/2002 | Richman |
| 6,744,793 B2 | 6/2004 | Stoner et al. |
| 6,844,554 B2 | 1/2005 | Karlsson |
| 6,853,452 B1 | 2/2005 | Laufer |
| 7,005,645 B2 | 2/2006 | Von Drasek et al. |
| 7,022,993 B1 | 4/2006 | Williams, II |
| 7,132,658 B2 | 11/2006 | Weckstrom et al. |
| 7,229,833 B1 | 6/2007 | Andersson |
| 7,248,755 B2 | 7/2007 | Sappey et al. |
| 7,251,034 B2 | 7/2007 | Kluczynski et al. |
| 7,288,766 B2 | 10/2007 | Uchida et al. |
| 7,326,931 B2 | 2/2008 | Frodl et al. |
| 7,339,669 B2 | 3/2008 | Matthiessen et al. |
| 7,385,681 B2 | 6/2008 | Ninomiya et al. |
| 7,460,567 B2 | 12/2008 | May |
| 7,492,980 B2 | 2/2009 | McCarthy et al. |
| 7,605,370 B2 | 10/2009 | Russell |
| 7,646,987 B2 | 1/2010 | Killinger |
| 7,705,988 B2 | 4/2010 | Richman |
| 7,723,685 B2 | 5/2010 | Arno |
| 7,728,977 B2 | 6/2010 | Sutton et al. |
| 7,939,022 B2 | 5/2011 | Theil |
| 7,969,576 B1 | 6/2011 | Buckley et al. |
| 8,080,798 B2 | 12/2011 | Russell |
| 8,085,301 B2 | 12/2011 | Hill, Jr. et al. |
| 8,193,502 B2 | 6/2012 | Hodgkinson et al. |
| 2002/0135762 A1 | 9/2002 | Wang et al. |
| 2003/0206325 A1* | 11/2003 | Sachse ............... G01N 21/3504 359/246 |
| 2010/0078563 A1 | 4/2010 | Haveri et al. |
| 2010/0264315 A1 | 10/2010 | Okada et al. |
| 2010/0301214 A1* | 12/2010 | Jonsson ............ G01N 21/3518 250/332 |
| 2012/0091346 A1 | 4/2012 | Bitter et al. |
| 2012/0103065 A1 | 5/2012 | Muehleisen |

OTHER PUBLICATIONS

Written Opinion for application PCT/US2014/011030 dated May 21, 2014, 6 pages.

* cited by examiner

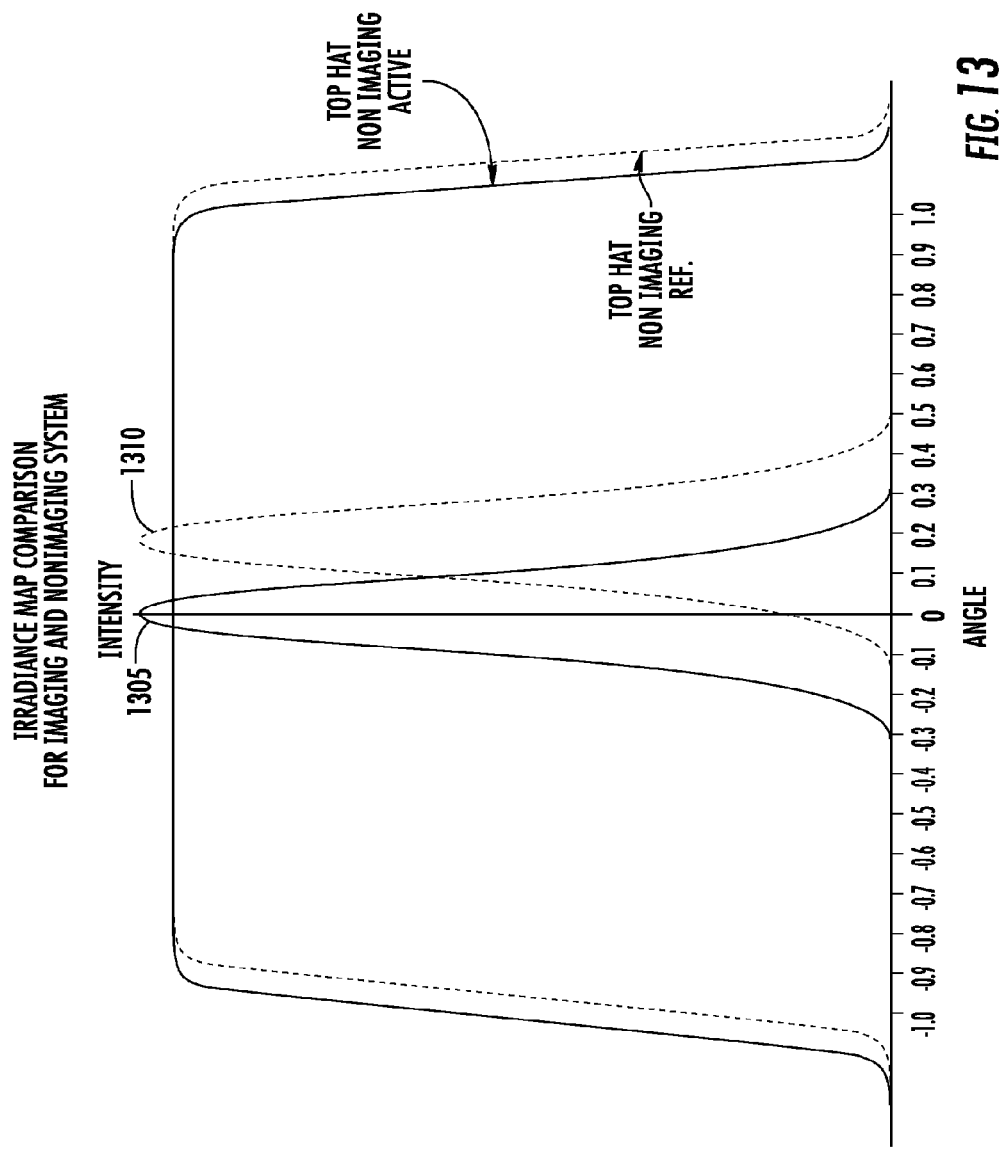

OPEN PATH GAS DETECTOR

FIELD

The present teachings relate to devices for, and methods of, open path gas detection.

BACKGROUND

The use of non-dispersive infrared spectroscopy to detect hydrocarbon gases is well established. It essentially involves transmitting infrared radiation along a path in an area being monitored; the wavelength of the infrared radiation is chosen so that it is absorbed by the gas of interest (hereafter called the "target gas"), but not substantially absorbed by other gases in the atmosphere of the area being monitored. The intensity of the radiation that has passed along the path in the area being monitored is measured and the attenuation in the intensity of the radiation gives a measure of the amount of target gas in the monitored area.

However, factors other than absorption by the target gas also attenuate the infrared radiation, including obscuration of the detecting beam, atmospheric scattering of the radiation, contamination of the lens surfaces, e.g. by dirt or condensation, and ageing of components. The reliability of infrared gas detectors is significantly improved by the use of a reference wavelength band; such a reference is usually infrared radiation at a different wavelength which ideally is a wavelength at which the target gas does not exhibit significant absorption. Radiation at more than one reference wavelength may be used; likewise more than one target wavelength may be used. Measuring the ratio between the signal obtained at the wavelength(s) where the target gas does absorb (the "sample" wavelength(s)) and the signal obtained at the wavelength(s) where the target gas does not significantly absorb (the "reference" wavelength(s)) more accurately measures the attenuation caused by environmental conditions because in most cases the signal at the reference wavelength(s) and the signal at the sample wavelength(s) will both be similarly affected by effects (other than the presence of target gas) that attenuate the radiation.

Usually, there are separate transmitter and receiver units at opposite ends of a straight beam path. Alternatively, the source and receiver are combined, and the beam bounced off a retroreflector at the far end of the measurement path. For portable use, detectors have also been made which use a remote object having suitable natural albedo in place of the retroreflector. The presence of a chosen gas (or class of gases) is detected from its absorption of a suitable infrared wavelength in the beam. Rain, fog etc. in the measurement path can also reduce the strength of the received signal, so it is usual to make a simultaneous measurement at one or more reference wavelengths. The quantity of gas intercepted by the beam is then inferred from the ratio changes of the signal losses at the measurement and reference wavelengths. The calculation is typically carried out by a microprocessor which also carries out various checks to validate the measurement and prevent false alarms.

Current open path gas detectors use an imaging optical system including a beam splitter to provide a signal for each detector where each detector has a dedicated bandpass interference filter to allow the appropriate wavelength to be transmitted to the intended detector. In this arrangement using a beam splitter, signal loss is 50% in each channel since half of the beam is sent to each detector. This arrangement is sensitive to slight misalignment between the dual optical channels that can lead to non-uniform images on the two detectors and erroneous gas determinations. Even small changes in alignment (<0.1 degree) or partial beam blockage) between the optical transmitter and receiver can lead to incorrect performance since the radiation cannot be accurately received on the misaligned photodiodes.

What is needed is an improved open path gas detection system that allows operation notwithstanding larger misalignment of the transmitter and the receiver and partial beam blockage of the transmitter and the receiver.

DESCRIPTION OF DRAWINGS

The accompanying drawings, which are incorporated in and constitute a part of this specification, illustrate implementations of the present teachings and together with the description, serve to explain the principles of the present teachings. In the figures:

FIG. 13 shows an irradiance map that illustrates the optical performance of an imaging and non-imaging optical system as a measure of the intensity over the angle of misalignment.

DETAILED DESCRIPTION

Figure 1:
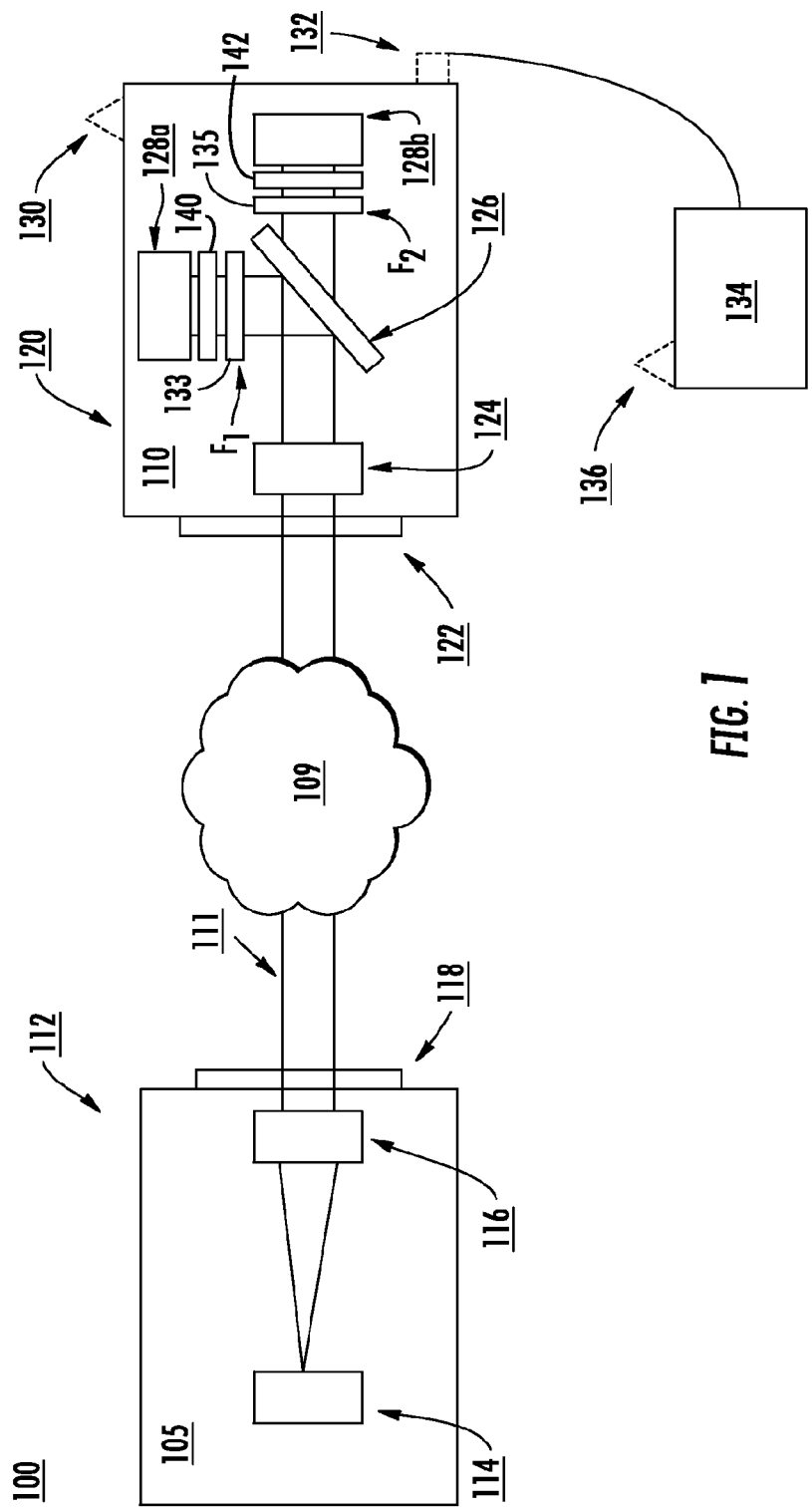
FIG. 1 is an example schematic representation of an open path gas detection system according implementation of the disclosure.

Reference will now be made in detail to example implementations of the present teachings, which are illustrated in the accompanying drawings. Where possible the same reference numbers will be used throughout the drawings to refer to the same or like parts.

In implementations, the open path gas detection system can include a receiving unit with either an imaging or a non-imaging optical system. The imaging system implementation provides a crisply formed image of the distant transmitter light source. In the non-imaging system implementation, uniform illumination can be provided with a non-imaging Kohler lens arrangement. In this non-imaging Kohler lens arrangement, the shape of the light pattern falling on the photodiodes is called "Top Hat Illumination" from the broad flatly illuminated region of light. This illumination shape can help reduce or eliminate output signal instability that is caused as the light source arc wanders which moves the hot spot around the objective back focal plane. Also, this illumination shape can help eliminate the spatial and temporal change of intensity on the active area of the photodiodes and provides stable detection signals. As a result, the illumination intensity falling on the photodiode can be improved using non-imaging Kohler illumination optics, which can tolerate misalignments of up to ±1.5 degrees of optical axis misalignment. In contrast, conventional imaging systems with the same object lens only allow a much smaller amount of misalignment. The Kohler non-imaging lens arrangement can also reduce or prevent false alarms resulting from partial beam block caused by birds, people, or equipment moving through the optical beam.

In implementations, the open path gas detection system can use a wavelength-division multiplexing (WDM) filter to separate input beam into two wavelengths. This arrangement using the WDM filter doubles signal strength in each channel compared to conventional beam splitter by using a wavelength selective filter at different wavelengths, wherein the first wavelength is reflected by the WDM filter while the second wavelength is transmitted through the WDM filter.

In implementations, the open path gas detection system can be operable to detect multiple gases by cascading WDM filters with non-overlapping filter band passes and additional photodiodes.

Additionally, in implementations, as field alignment is degraded from independent motion of the transmitter and receiver, such as flexing in a large marine vessel in rough seas, the peripheries of the imaging system may experience significant differential edge effects. This leads to spatial and temporal change of intensity on the active area of the photodiodes. Thus, the instrument may indicate inaccurately. To mitigate this effect, the active/reference ratio can be adjusted by a non-imaging system top hat illumination scheme with a reference channel aperture which results in upward ratio trajectory as the optical axis is moved beyond the edge of proper operation. This direction will not cause a false gas alarm during periods of optical axis instability.

FIG. 1 is an example schematic representation of an open path gas detection system according implementation of the disclosure. While FIG. 1 illustrates various components, modules, and/or features of open path gas detection system, one skilled in the art will realize that these components, modules, and/or features are exemplary and that the open path gas detection system can include any number and type of components, modules, and/or features.

As illustrated in FIG. 1, open path gas detection system 100 can include transmitter unit 105 that is operable to provide radiation along a path to receiver unit 110. The path can include area 109 where target gas is present and area 111 were clean air is present. In implementations, transmitter unit 105 and receiver unit 110 can include similar components and each can be operable to both perform transmitting and receiving functions and be operable to be a transceiver. The use of the words "transmitter," "transmitting," "receiver," "receiving," and similar terminology is merely to describe the functionality of the components of the open path gas detector system. In one implementation, transmitter unit 105 can be operating in transmitter mode, but could also function as a receiver. The same is true of receiver unit 110.

Transmitter unit 105 can include housing 112 operable to support and house radiation source 114, one or more conditioning, focusing, and/or directing optical components or transmitter optical components 116, and aperture 118. Radiation source 114 can be operable to produce radiation in a variety of wavelengths and/or intensities. Transmitter optical components 116 can be operable to direct, modify, condition, or change the radiation from radiation source 114. Radiation source 114 and/or transmitter optical components can be chosen depending on the particular circumstances and environments in which the open gas detector system 100 is being used. For example, radiation source 114 can include a tunable laser diode that is operable to produce a beam of infrared radiation in a very narrow wavelength band. Additionally and/or alternatively, radiation source 114 can be operable to produce radiation at one or more wavelengths and having wide or narrow wavelength linewidths. The tunable laser diode is just one example for the radiation source 114. Other suitable radiation sources can be used. Transmitter optical components 116 can include, for example, a steerable optical element, such as a steerable mirror, and one or more collimation optics that can receive radiation from radiation source 114 and direct the radiation along a measurement path that can have a substantial length, for example 20 to 1,000 m, to receiver unit 110. Transmitter unit 105 can include one or more controllers (not shown) that are operable to control a particular operating mode of radiation source 114 and/or transmitter optical components 116, wherein the operating mode can include a predetermined wavelength range, line width range, and/or intensity range of the radiation from transmitter unit 105.

The wavelength or range of wavelengths of the radiation produced by radiation source 114 can be selected such that the radiation is of a frequency that would be absorbed by one or more target gases along the measurement path. In implementations, the output wavelength of radiation source 114 can be varied to scan across the gas absorption band of one or more target gases.

Receiver unit 110 can include housing 120 operable to support and house aperture 122, one or more lens components (optional) 124, optical component 126 operable to separate the incident radiation, such as a wavelength-division multiplexing (WDM) filter or beam splitter, and detectors 128a, 128b. Aperture 122 can be sized to allow a desired amount of radiation to enter into housing 120. Filtering components $F_1$ 133 and $F_2$ 135 can be interference bandpass filters that are operable to filter out radiation in wavelengths that are not of interest. Radiation can be received through aperture 122, pass through lens components 124 and WDM filter 126 and be directed onto detectors 128a, 128b. Radiation can be received through aperture 122 and pass WDM filter 126 and be directed onto detectors 128a, 128b that produces a signal that gives a measure of the intensity of the radiation incident on the detectors 128a, 128b. The signal is processed to extract the ratio of the active and reference to determine if the target gas is present. The signal can be transmitted to wireless transceiver 136 on controller 134 by wireless transceiver 130 on receiver unit 110 or by wired connection 132 for processing, analysis, and/or reporting.

In implementations, receiver unit 110 can be configured using imaging and non-imaging optical components, which are discussed further below. Non-imaging optical systems are operable to optimize the transfer of optical energy between a source and a receiver. The designs are based on some portion or combination of: the edge ray principle; the flow line method; the simultaneous multiple surface design (SMS); the Milano method; the compound parabolic concentrator; or Kohler integration. Conservation of etendue is a characteristic of these methods. All of these techniques will be familiar to those skilled in the art.

For example, when the receiver unit 110 comprises non-imaging optical components, the receiver unit 110 can include one or more beam-shaping optical elements 140 and 142 that are operable to change the shape (profile) of the beam or homogenize the radiation such that radiation is provided to the photosensitive elements of detectors 128a, 128b having a nearly uniform illumination profile. Beam-shaping optical elements 140 and 142 can be arranged either in front of or behind filters 133 and 135 or in front of the active and the reference photodiodes depending on the particular arrangement of components within the receiver unit 110. For example, the nearly uniform illumination can have a top-hat-like or flat profile making up most of the profile width. A variety of optical elements can comprise the one or more beam-shaping optical elements 140 and 142 including, but not limited to, Kohler lenses, Fly's Eye condensers Micro-lens Arrays or Micro-lens Beam Homogenizers, Faceted Tubes, and compound parabolic devices. Other suitable beam-shaping/homogenizing optical elements can also be used. The descriptions below describe receiver units with a Kohler lens to provide the top-hat-like illumination profile. However, this is merely exemplary and any of the references below to the Kohler lens can be substituted for any of the suitable beam-shaping/homogenizing optical elements discussed above.

In implementations, the operation and functionality associated with transmitter unit 105 and receiver unit 110 can be provided in a single transceiver device. In implementations, both transmitter unit 105 and receiver unit 110 can be a single transceiver device. In implementations, transmitter unit 105 can be a single transceiver device, operable to direct radiation along a path to a reflecting device, such as a retroreflector, object(s) with a suitable natural albedo, or other suitable reflecting devices.

By way of a non-limiting example, as flammable hydrocarbon gases intersect the light beam between the two modules, certain IR wavelengths are absorbed by the gas, while other IR wavelengths are not. The amount of IR absorption is determined by the concentration of the hydrocarbon gas. One or more optical detectors and associated electronics located in the receiver module can measure the absorption. The change in intensity of the absorbed light (active signal) is measured relative to the intensity of light at a non-absorbed wavelength (reference signal). The microprocessor computes the gas concentration and converts the ratio value into an analog or digital output signal, which is then communicated to external control and annunciation systems.

For example, for certain common hydrocarbon gases, suitable peak absorption wavelengths include, but are not limited to, 1.6 µm, 2.3 µm, and 3.3 µm. Thus, for an exemplary embodiment of an apparatus in accordance with the principles of the present teachings that is to detect combustible hydrocarbons, it may be suitable to select a first and/or a second spectral band to be centered on or near 1.6 µm, 2.3 µm, and/or 3.3 µm. However, this is exemplary only. Other wavelengths may be equally suitable, both for hydrocarbon gases and for non-hydrocarbon gases. The center wavelengths of the first and second spectral bands may vary considerably from embodiment to embodiment. The precise wavelength sensitivities appropriate for a particular embodiment will depend on a variety of factors, including but not limited to the type or types of gas that a given embodiment is meant to detect. A variety of bandwidths may be suitable for the first and second spectral bands. In an embodiment of a gas detector in accordance with the principles of the present teachings that is adapted to detect hydrocarbon gas, the first and second spectral bands may have bandwidths of approximately 0.10 µm and 0.30 µm, respectively. However, these bandwidths are exemplary only. For example, for certain alternative embodiments, a bandwidth of approximately 30 nm for the first spectral band and approximately 100 nm for the second spectral band may be suitable.

The present teachings are not limited to detection of hydrocarbon gases only, or to detection of flammable gases only. Embodiments of the present teachings may be suitable for detecting substantially any gas that absorbs and/or transmits IR radiation at a different rate than the surrounding environment, atmosphere, or gas. For example, certain embodiments of the present teachings may be suitable for detecting gases that pose a risk of environmental degradation, such as refrigerants or fire suppressants. Likewise, certain embodiments may be suitable for detecting toxic or carcinogenic gases, such as industrial byproducts. More particularly, embodiments of the present teachings may be suitable for detecting gases including but not limited to chlorinated fluorocarbons (CFCs), hydrogen sulfide, halogens, bromine, hydrogen cyanide, etc. In addition, embodiments of the present teachings may be suitable for simultaneously and independently detecting more than one type of gas. Further, multiple gases can be detected using additional WDM filters that are configured to allow detection using multiple channels at different wavelengths.

By way of a non-limiting example, a computer processor can be used to analyze the intensity measured by a detector unit at a wavelength of interest and compared by the processor to the intensity of light detected by the detector unit at a reference wavelength where no gas absorption of IR occurs. This method of detection is commonly known as Differential Optical Absorption Spectroscopy (DOAS). This DOAS methodology is a simple, inexpensive means of determining a concentration of a gas of interest. Alternatively, again using a computer processor, the intensity measured by a detector unit at a desired wavelength for an interval of time, followed by measuring light at the detector unit for an interval of time at the same wavelength with additionally a gas cell of known concentration of gas that absorbs light of the same wavelength can also be used as a methodology to determine a concentration of a gas of interest. This method of detection is commonly known as Gas Filter Correlation Radiometry (GFCr). GFCr has the potential to provide improved precision and accuracy because it allows for the constant referencing of a measurement to a known concentration of the gas of interest.

Figure 2:
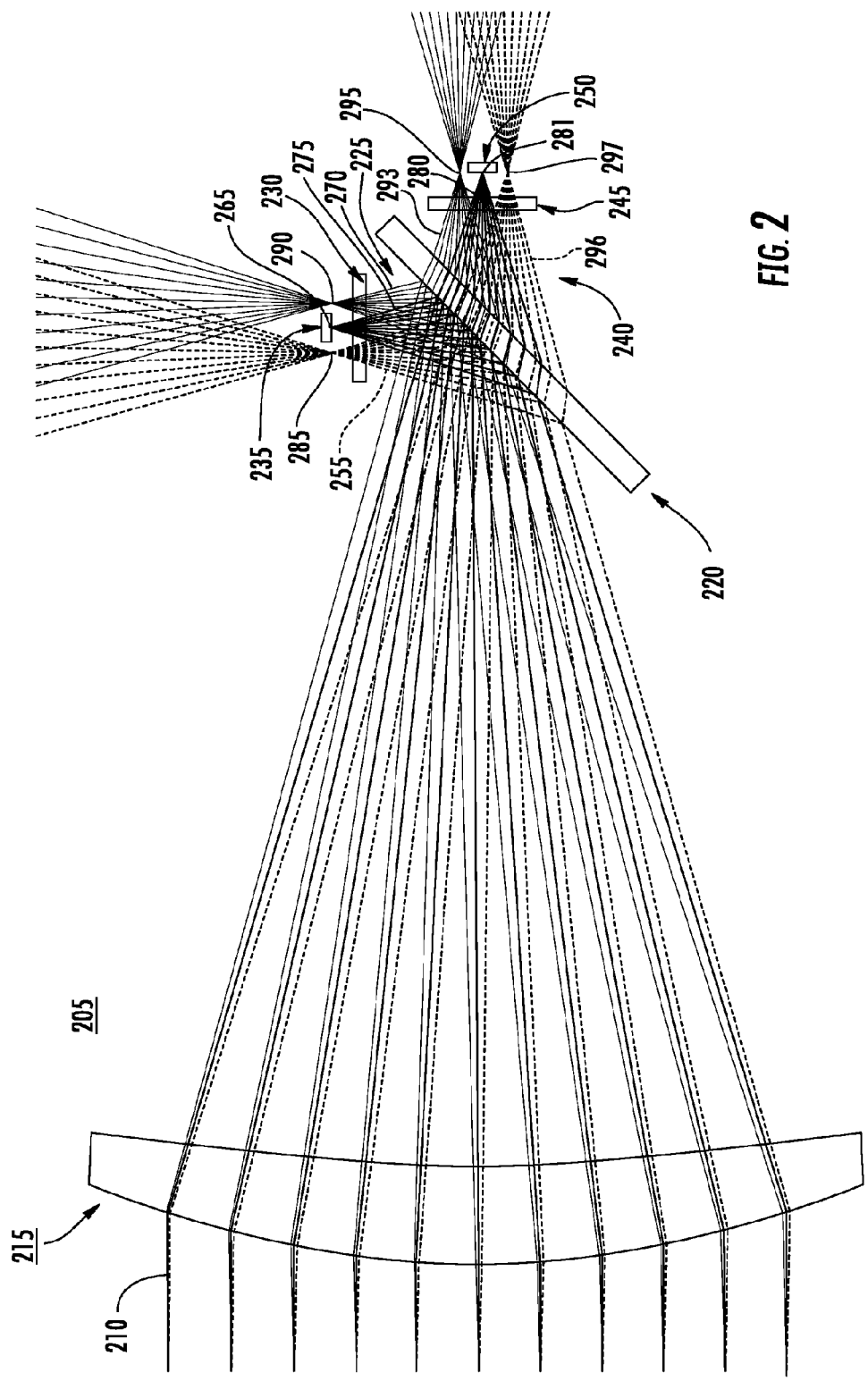
FIG. 2 shows example components of receiver unit 110 comprising imaging system 205 comprising a WDM filter in greater detail in accordance with implementations of the present disclosure.

FIG. 2 shows example components of receiver unit 110 comprising imaging system 205 comprising a WDM filter in greater detail in accordance with implementations of the present disclosure. While FIG. 2 illustrates various components, modules, and/or features of receiver unit 110, one skilled in the art will realize that these components, modules, and/or features are exemplary and that the receiver unit 110 can include any number and type of components, modules, and/or features.

As illustrated in FIG. 2, optical components of receiver unit 110 can comprise an imaging system 205, whereby radiation 210 is received through aperture 122 of receiver unit 110 and is imaged onto detectors or photodiodes 235 and 250. Objective lens 215 is arranged near aperture 122 within receiver unit 110 to collect and direct radiation 210 onto optical element 220. In implementations, optical element 220 can be a wavelength-division multiplexing (WDM) filter that is operable to separate radiation 210 by wavelength. For example, WDM filter can be operable to separate radiation 210 into a first wavelength portion 225 and a second wavelength portion 240. First wavelength portion 225 is reflected through first filter 230, for example a reference filter, and onto first photodiode 235, for example reference photodiode. Second wavelength portion 240 is transmitted through second filter 245, for example active filter, and onto second photodiode 250, for example active photodiode. As used throughout this disclosure, the term "active" refers to the fact that infrared radiation transmitted by this filter is affected by the presence of the gas to be detected via absorption, whereas the term "reference" refers to the fact that infrared radiation transmitted by this filter is not affected by the presence of the gas to be detected. In implementations, the two filters by themselves do not provide for identification or discrimination of the gas type or species, i.e., the detector (photodiodes) will respond to any gas that absorbs at the active wavelength without informing the user which type of gas has crossed the optical beam path. In implementations, the filters can include more than one filter to allow identification of a type and amount of gas within a family of gases. In implementations, the WDM filter can be configured to allow multiple channels at different wavelengths to detect multiple gases.

With the arrangement of imaging system 205, radiation cannot be received on photodiodes 235 and 250 of receiver unit 110 if offset by ±1°, represented by 255 and 270, respectively, from the central or zero offset position 275 for first wavelength portion 225 and offset radiation of ±1°, represented by 293 and 296, respectively, from the central or zero offset position 280 for second wavelength portion 240, and cannot be operable to resolve signals from photodiodes 235 and 250 since the focal point 285 and 290 from first wavelength portion 225 and focal points 295 and 297 from second wavelength portion 240 missed the active area of the photodiodes 235 and 250.

Figure 3:
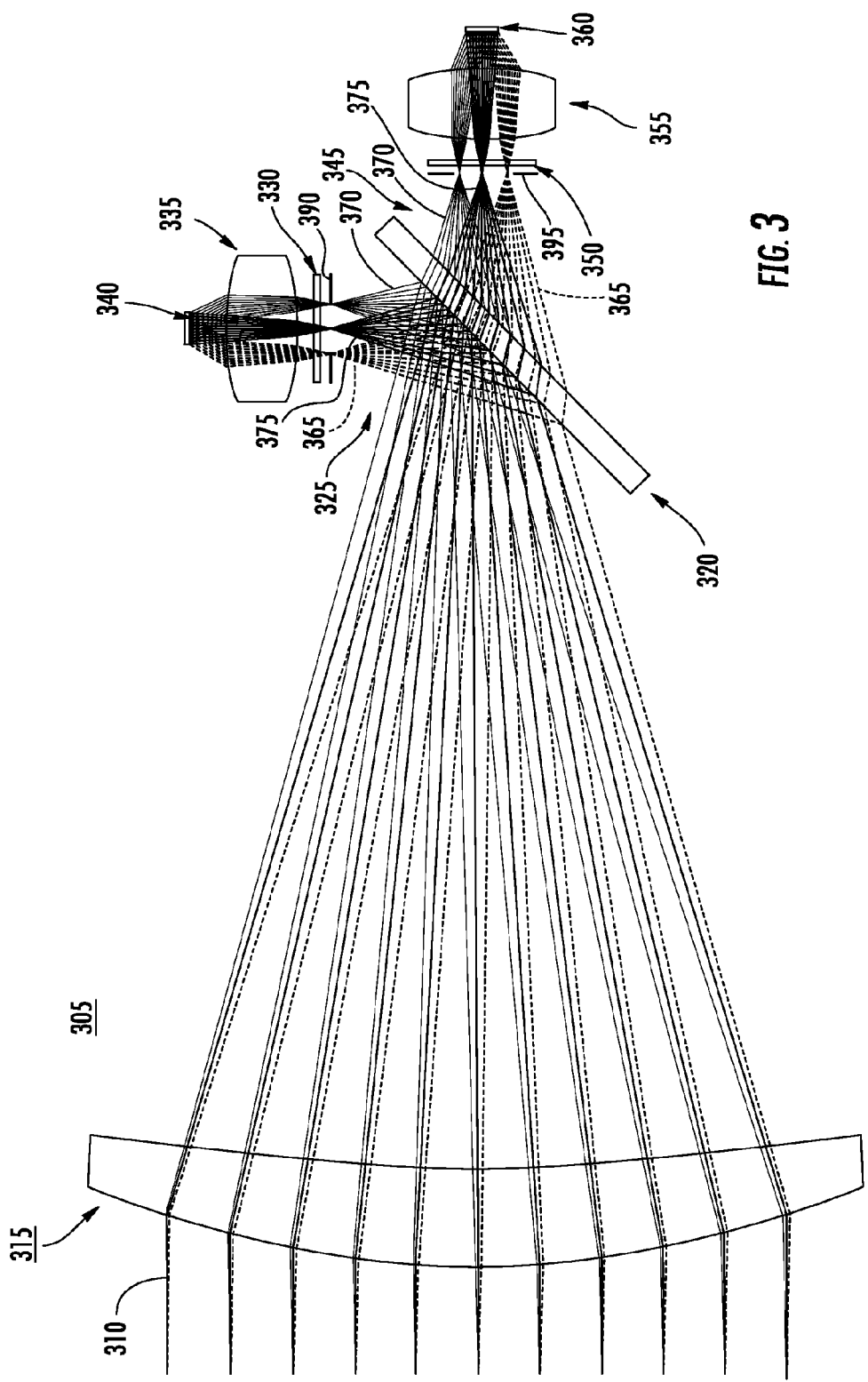
FIG. 3 shows example components of receiver unit 110 comprising non-imaging system 305 comprising a beam splitter in accordance with implementations of the present disclosure.

FIG. 3 shows example components of receiver unit 110 comprising non-imaging system 305 comprising a beam splitter in accordance with implementations of the present disclosure. While FIG. 3 illustrates various components, modules, and/or features of receiver unit 110, one skilled in the art will realize that these components, modules, and/or features are exemplary and that the receiver unit 110 can include any number and type of components, modules, and/or features.

As illustrated in FIG. 3, optical components of receiver unit 110 comprise non-imaging system 305, whereby radiation 310 is received through aperture 122 and objective lens 315 of receiver unit 110 and is provided to detectors or photodiodes 340 and 360. Objective lens 315 is arranged near aperture 122 within receiver unit 110 to collect and direct radiation 310 onto optical element 320. In implementations, optical element 320 can be a beam splitter that is operable to separate radiation 310 into first or reflected portion 325 and second or transmitted portion 345. In implementations, the beam splitter can be a 50/50 beam splitter where radiation 310 that is incident onto the beam splitter can be divided evenly to produce first or reflected portion 325 and second or transmitted portion 345 having equal intensities. First or reflected portion 325 is direct through first filter 330, for example reference filter, and Kohler lens 335, for example reference Kohler lens, onto first photodiode 340, for example reference photodiode. Second or transmitted portion 345 is directed through second filter 350, or active filter, and second Kohler lens 355, for example active Kohler lens, onto second photodiode 360, for example active photodiode. Field stop 390 can be included near an entrance face of first filter 330 and field stop 395 can be included near an entrance face of second filter 350. Field stops 390 and 395 can function to control the amount of radiation that reaches filters 330 and 350 and is thus received onto photodiodes 340 and 360. Field stop 390 (reference field stop) and field stop 395 (active field stop) may be adjustable depending on the particular use of the receiver unit and can be customizable to meet particular requirements. For example, some applications need ±1° field of view to limit adjacent transmitter signals from getting into the receiver unit while others could tolerate a ±1.5° field of view, which can have a bigger field misalignment tolerance and a longer maintenance call period. In general, a large field of view (FOV) of the receiver unit can allow for larger transmitter-to-receiver beam misalignments during environmental changes, which can lead to increased interval for maintenance and more effective transmitter detection during initial field installation alignment. In implementations, the diameter of active field stop 395 can be bigger than the diameter of reference field stop 390. In this implementation, false or negative gas readings can be obtained if the field alignment is off the specification. With the arrangement of non-imaging system 305, radiation can be received by receiver unit 110 offset by ±1°, represented by 365 and 370, respectively, from the zero offset position 375, and still be operable to resolve signals from photodiodes 340 and 360. The arrangement of FIG. 3 offers numerous advantages over conventional designs by including an increased field of view (FOV) of the receiver unit, prolonging a service interval (amount of time between service visits) of the receiver unit, and increasing the output signal stability.

Figure 4:
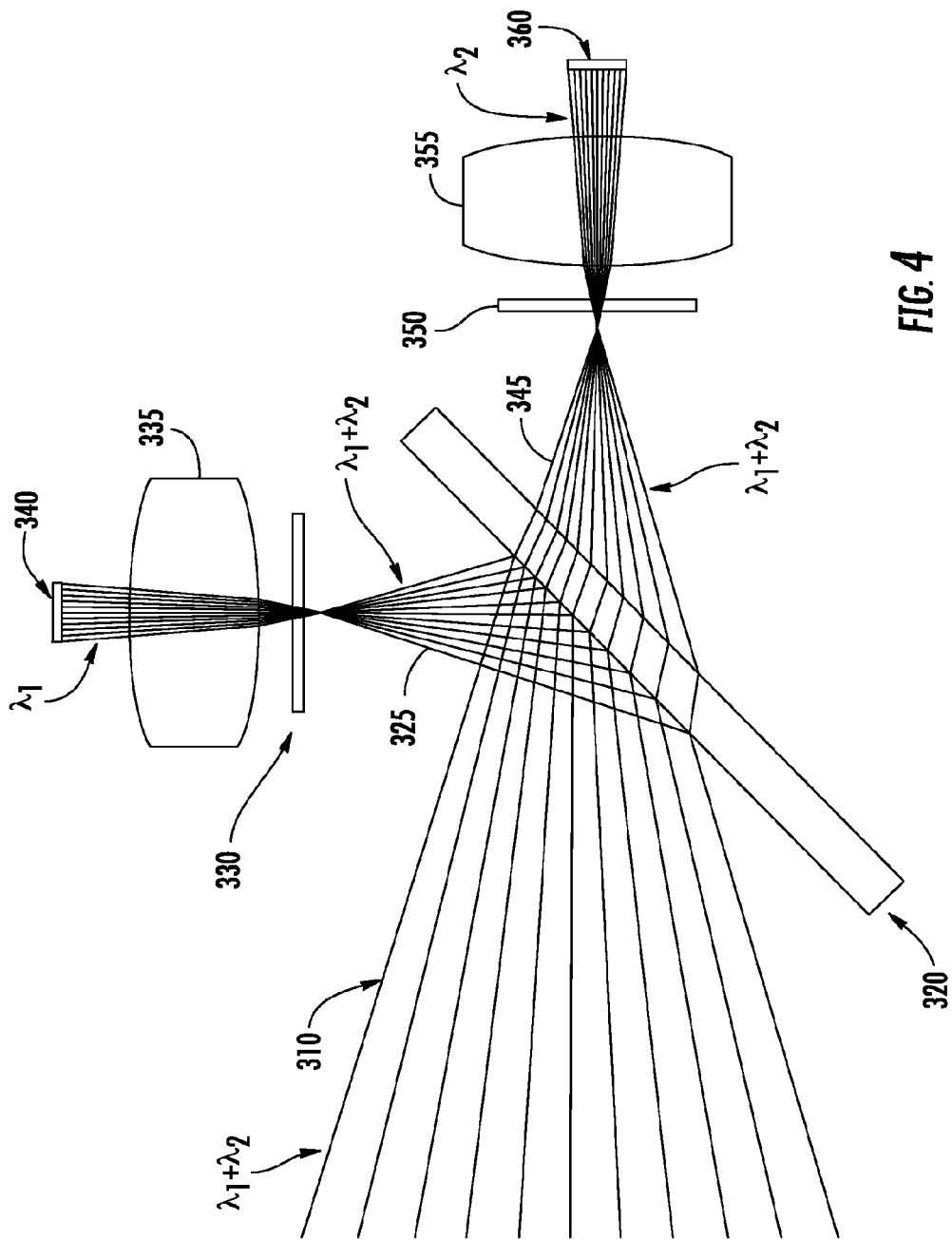
FIG. 4 shows a close up of certain components non-imaging system 305 of receiver unit 110 of FIG. 3.

FIG. 4 shows a close up of certain components in non-imaging system 305 of receiver unit 110 of FIG. 3. Incoming radiation 310 to receiver unit 110 can include radiation having more than one wavelength, for example, radiation 310 including wavelengths $\lambda_1$ and $\lambda_2$. For example, radiation 310 can include radiation having a first wavelength $\lambda_1$ of 2.125 µm and a second wavelength $\lambda_2$ of 2.315 µm. Other suitable wavelengths can be chosen depending on the operating conditions of the open path gas detector system. Radiation 310 is incident on the beam splitter 320, which is operable to split radiation 310 into first or reflected portion 325 and second or transmitted portion 345, wherein both first or reflected portion 325 and second or transmitted portion 345 contain radiation having wavelengths of both $\lambda_1$ and $\lambda_2$, for example wavelengths including 2.125 µm and 2.315 µm. For example, beam splitter 320 can be a 50% beam splitter where 50% of the radiation 310 is reflected to the reference channel and 50% of the radiation 310 is transmitted to the active channel. Both portions 325 and 345 of the radiation separated by beam splitter 320 will both contain radiation having wavelengths $\lambda_1$ and $\lambda_2$, for example wavelengths including of 2.125 µm and 2.315 µm. First filter 330 and second filter 350 can be operable to select out a desired wavelength or range of wavelengths by blocking (i.e. absorbing) and/or reflecting one wavelength or range of wavelengths and transmitting another wavelength or range of wavelengths. In the example, first filter 330 is operable to transmit radiation having a wavelength of about $\lambda_1$, for example about 2.125 µm and second filter 350 is operable to transmit radiation having a wavelength of about $\lambda_2$, for example about 2.315 µm. The radiation having the wavelength of about for example about 2.125 µm is then provided to first Kohler lens 335 and first photodiode 340 and the radiation having the wavelength of about $\lambda_2$, for example about 2.315 μm is provided to second Kohler lens 355 and second photodiode 360.

Figure 5:
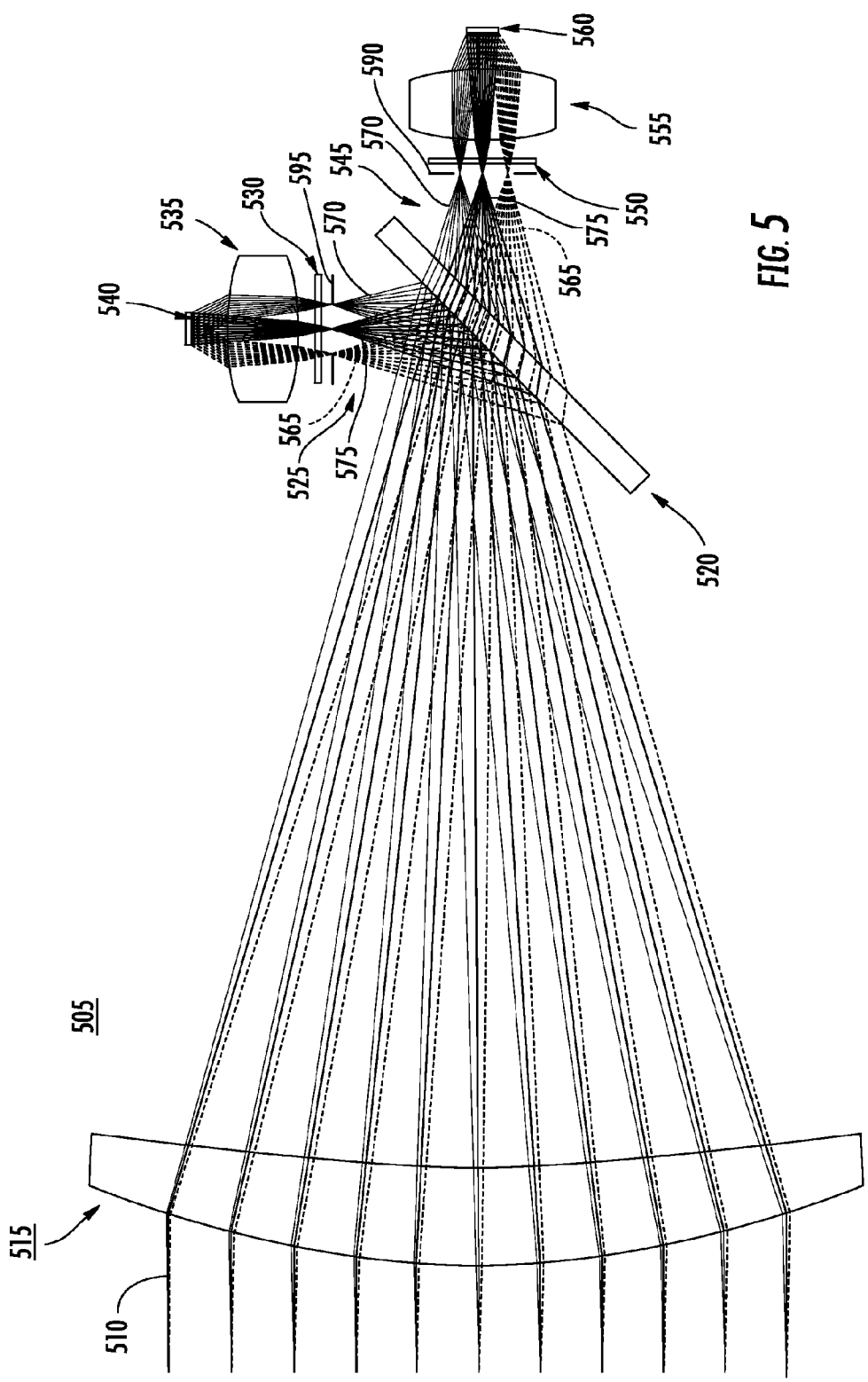
FIG. 5 shows example components of receiver unit 110 comprising non-imaging system 505 comprising WDM filter in accordance with implementations of the present disclosure.

FIG. 5 shows example components of receiver unit 110 comprising non-imaging system 505 comprising WDM filter in accordance with implementations of the present disclosure. While FIG. 5 illustrates various components, modules, and/or features of receiver unit 110, one skilled in the art will realize that these components, modules, and/or features are exemplary and that the receiver unit 110 can include any number and type of components, modules, and/or features.

As illustrated in FIG. 5, optical components of receiver unit 110 comprise non-imaging system 505, whereby radiation 510 is received through an aperture and objective lens 515 of receiver unit 110 and is provided to detectors or photodiodes 540 and 560. Objective lens 515 is arranged near aperture 122 within receiver unit 110 to collect and direct radiation 510 onto optical element 520. In implementations, optical element 520 can be a wavelength-division multiplexing (WDM) filter that is operable to separate radiation 510 by wavelength. For example, the WDM filter can be operable to separate radiation 510 into first wavelength portion 525 and second wavelength portion 545. First wavelength portion 525 is direct through first filter 530, for example reference filter, and first Kohler lens 535, for example reference Kohler lens, and onto first photodiode 540, for example reference photodiode. Second wavelength portion 545 is directed through second filter 550, for example active filter, and second Kohler lens 555, for example active Kohler lens, onto second photodiode 560, for example active photodiode. With the arrangement of non-imaging system 505, radiation can be received by receiver unit 110 offset by ±1° or larger, represented by 565 and 570, respectively, from the zero offset position 575, and still be operable to resolve signals from photodiodes 540 and 560. Field stops 590 and 595, which are similar to field stops 390 and 395, can also be included and function like those discussed in relation to FIG. 3.

Figure 6:
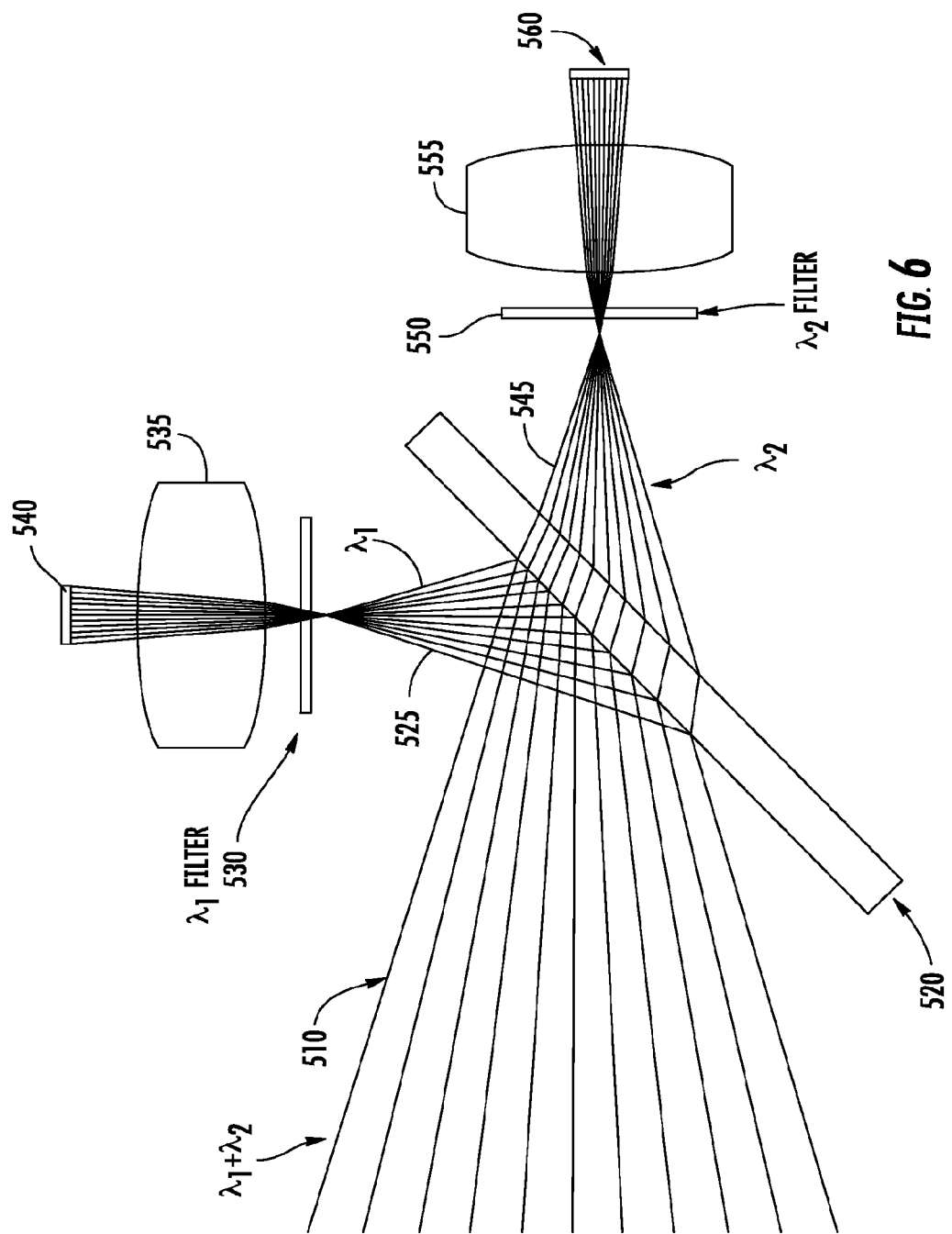
FIG. 6 shows a close up view of certain components non-imaging system 505 of receiver unit 110 of FIG. 5.

FIG. 6 shows a close up view of certain components of non-imaging system 505 of receiver unit 110 of FIG. 5. While FIG. 6 illustrates various components, modules, and/or features of receiver unit 110, one skilled in the art will realize that these components, modules, and/or features are exemplary and that the receiver unit 110 can include any number and type of components, modules, and/or features.

As illustrated in FIG. 6, the WDM filter 520 in combination with first filter 530 and second filter 550 of the receiver unit is operable to separate incident radiation 510 by wavelength. In the example shown, the WDM filter 520 is operable separate incoming radiation 510 containing both a first wavelength about $\lambda_1$ and a second wavelength about $\lambda_2$. For example, the first wavelength $\lambda_1$ can be about 2.125 μm and the second wavelength $\lambda_2$ can be about 2.315 μm. The WDM filter 520 can separate radiation 510 by reflecting approximately 100% of the first wavelength $\lambda_1$, for example 2.125 μm to the reference channel and transmitting approximately 100% of the second wavelength $\lambda_2$, for example 2.315 μm to the active channel. WDM filter directs a first wavelength portion $\lambda_1$ 525 of incident radiation 510 to first filter 530 and first Kohler lens 535 onto first photodiode 540 and directs second wavelength portion $\lambda_2$ 545 of incident radiation 510 to second filter 550 and second Kohler lens 555 onto second photodiode 560. First filter 530 and second filter 550 can be operable to select out a desire wavelength or range of wavelengths by blocking (i.e. absorbing) and/or reflecting one wavelength or range of wavelengths and transmitting another wavelength or range of wavelengths. In the example, first filter 530 is operable to transmit radiation having a first wavelength $\lambda_1$, for example, a wavelength of about 2.125 μm and second filter 550 is operable to transmit radiation having a second wavelength $\lambda_2$, for example, a wavelength of about 2.315 μm. The radiation having the first wavelength $\lambda_1$, for example, a wavelength of about 2.125 μm is then provided to first Kohler lens 535 and first photodiode 540 and the radiation having the second wavelength $\lambda_2$, for example, a wavelength of about 2.315 μm is provided to second Kohler lens 555 and second photodiode 560. The WDM filter can also function as discussed above in the arrangement of FIG. 2 with the beam splitter.

Figure 7:
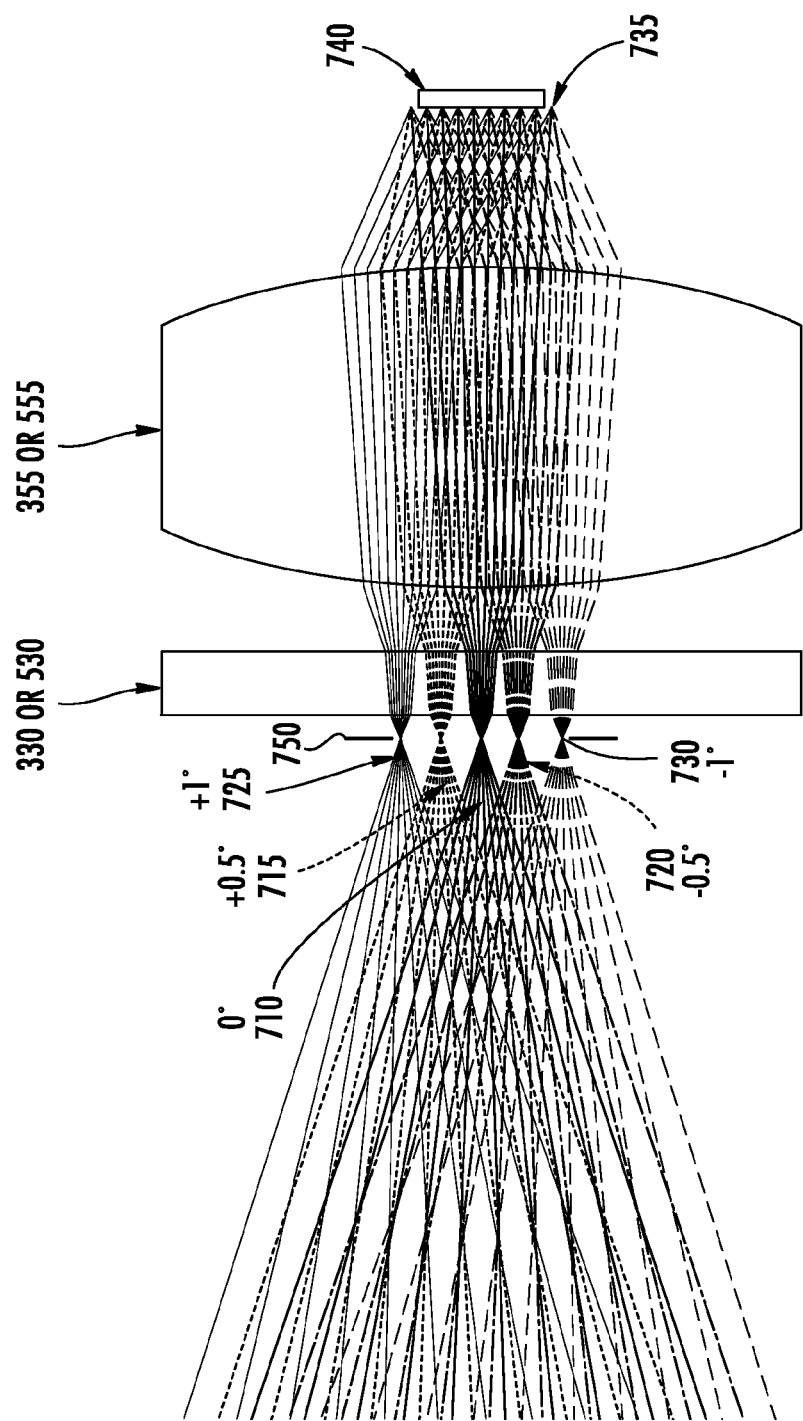
FIG. 7 shows close up view of certain components of the non-imaging optical systems of FIGS. 3 and 5.

FIG. 7 shows close up view of certain components of the non-imaging optical systems of FIGS. 3 and 5. While FIG. 7 illustrates various components, modules, and/or features of receiver unit 110, one skilled in the art will realize that these components, modules, and/or features are exemplary and that the receiver unit 110 can include any number and type of components, modules, and/or features.

As illustrated in FIG. 7, radiation is shown in five representative positions either entering first filter 330 or 530 and first Kohler lens 335 or 535 and onto an exemplary 1 mm diameter active area of photodiode 340 or 540. Likewise, this arrangement can be illustrative of radiation entering second filter 350 or 550 and second Kohler lens 355 or 555 and onto an exemplary 1 mm sized active area of photodiode 360 or 560. The five positions include a zero offset position (0°) 710, ±0.5° offset 715 and 720, respectively, and ±1° offset 725 and 730, respectively. The light spot 735 incident onto the active area of photodiode 740 tends to be larger than the size the active area of 740. For example, the diameter of the light spot 735 can be between about 1 mm and 1.5 mm. In this example, when the receiver unit 110 receives radiation having a ±1° misalignment onto a photodiode with a 1 mm diameter active region, the active region is still operable to receive the radiation completely. Thus, this arrangement allows alignment requirements during manufacturing, installation, and/or operation of the receiving unit to be eased. Field stop 750, which is similar to either of field stops 390 and 395, can also be included and function like those discussed in relation to FIG. 3.

Figure 8:
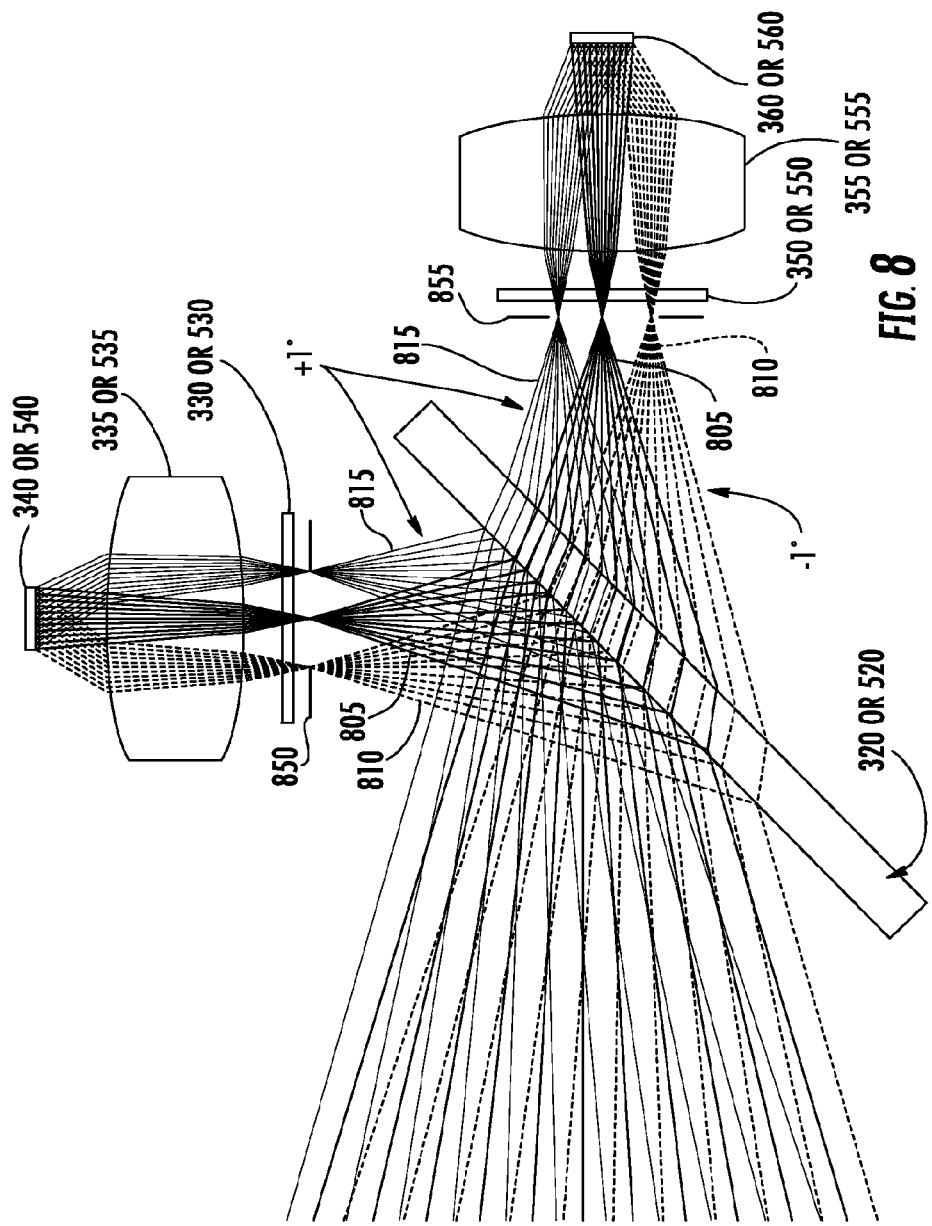
FIG. 8 shows a close up view of receiver unit similar to FIGS. 3 and 5 with incoming radiation in two states of misalignment.

FIG. 8 shows a close up view of a receiver unit similar to FIGS. 3 and 5 with incoming radiation in two states of misalignment. Zero offset radiation 805 is shown along with ±1° misalignment radiation 810 and 815, respectively, being separated by the beam splitter 320 of FIG. 3 or the WDM filter 520 of FIG. 5. A first radiation portion is provided to first filter 330 or 530 and first Kohler lens 335 or 535 and onto first photodiode 340 or 540 and a second radiation portion is provided to second filter 350 or 550 and second Kohler lens 355 or 555 and onto second photodiode 360 or 560 by the beam splitter 320 or the WDM filter 520. Stops 850 and 855, which similar to those stops 390 and 395, can also be included and function like those discussed in relation to FIG. 3. The arrangement of non-imaging optics allows for up to ±1° misalignment of the incoming radiation with no loss of signal quality on the photodiodes.

Figure 9:
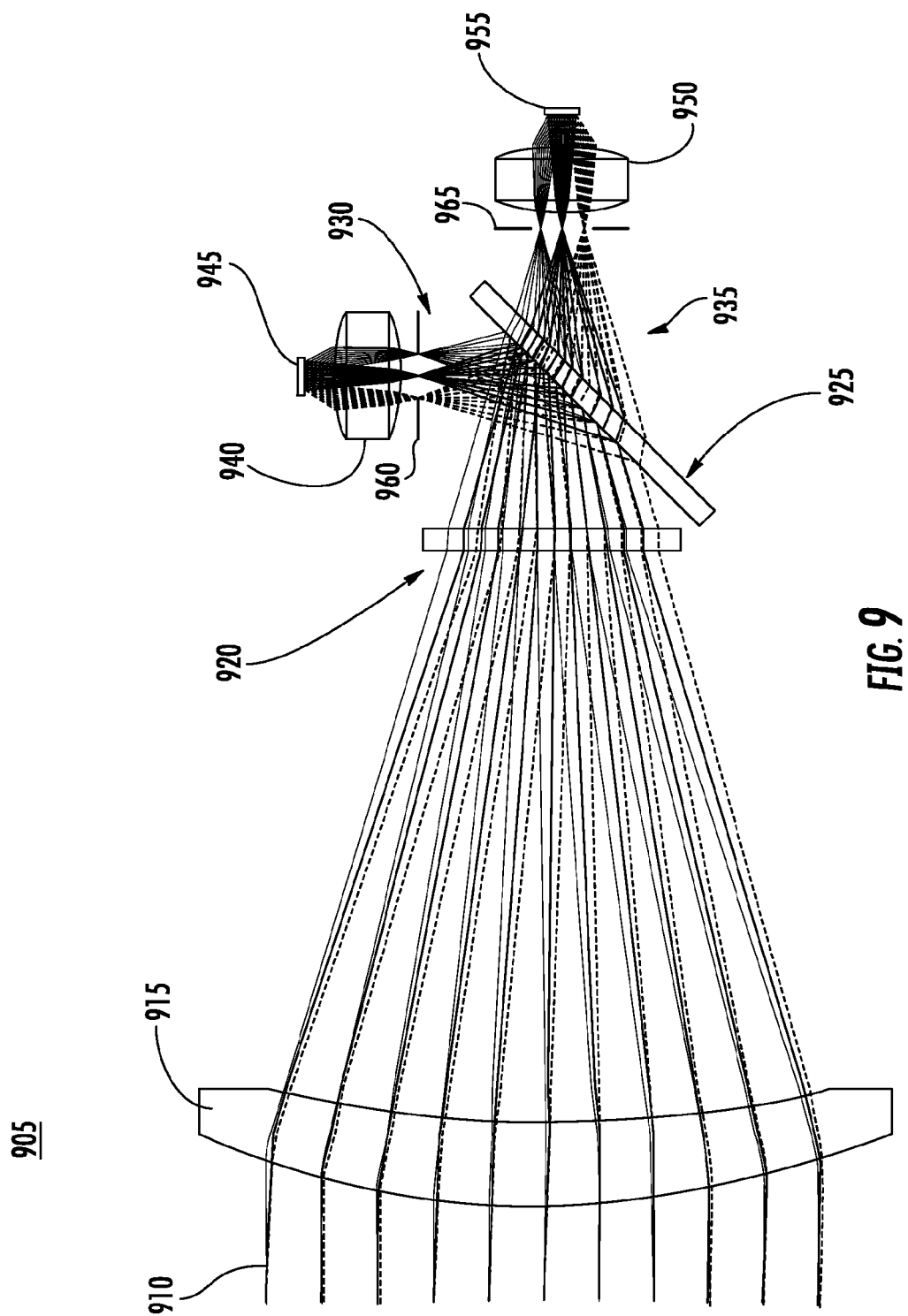
FIG. 9 shows another example of a receiver unit in accordance with implementations of the present disclosure.

FIG. 9 shows another example receiver unit in accordance with implementations of the present disclosure. While FIG. 9 illustrates various components, modules, and/or features of receiver unit 905, one skilled in the art will realize that these components, modules, and/or features are exemplary and that the receiver unit 965 can include any number and type of components, modules, and/or features.

As illustrated in FIG. 9, radiation 910 is received through an aperture and objective lens 915 of receiver unit 905 and is provided to detectors or photodiodes 945 and 955. Objective lens 915 is arranged near the aperture within receiver unit 965 to collect and direct radiation 910 onto optical elements 920 and 925. In implementations, optical element 920 can be a bandpass filter that is operable to transmit radiation having wavelengths, for example, between about a first wavelength $\lambda_1$ and about a second wavelength $\lambda_2$ and optical element 925 can be a wavelength-division multiplexing (WDM) filter that is operable to separate radiation 910 by wavelength. For example, the WDM filter can be operable to separate radiation 910 into first wavelength portion 930 and second wavelength portion 935. First wavelength portion 930 is direct through first Kohler lens 940, for example reference Kohler lens, and onto first photodiode 945, for example reference photodiode. Second wavelength portion 935 is directed through second Kohler lens 950 onto second photodiode 955, for example active photodiode. Stops 960 and 965, which similar to those stops 390 and 395, can also be included and function like those discussed in relation to FIG. 3. With the arrangement of non-imaging system 905, radiation can be received by receiver unit 905 offset by ±1° from the zero offset position and still be operable to resolve signals from photodiodes 945 and 955.

Figure 10:
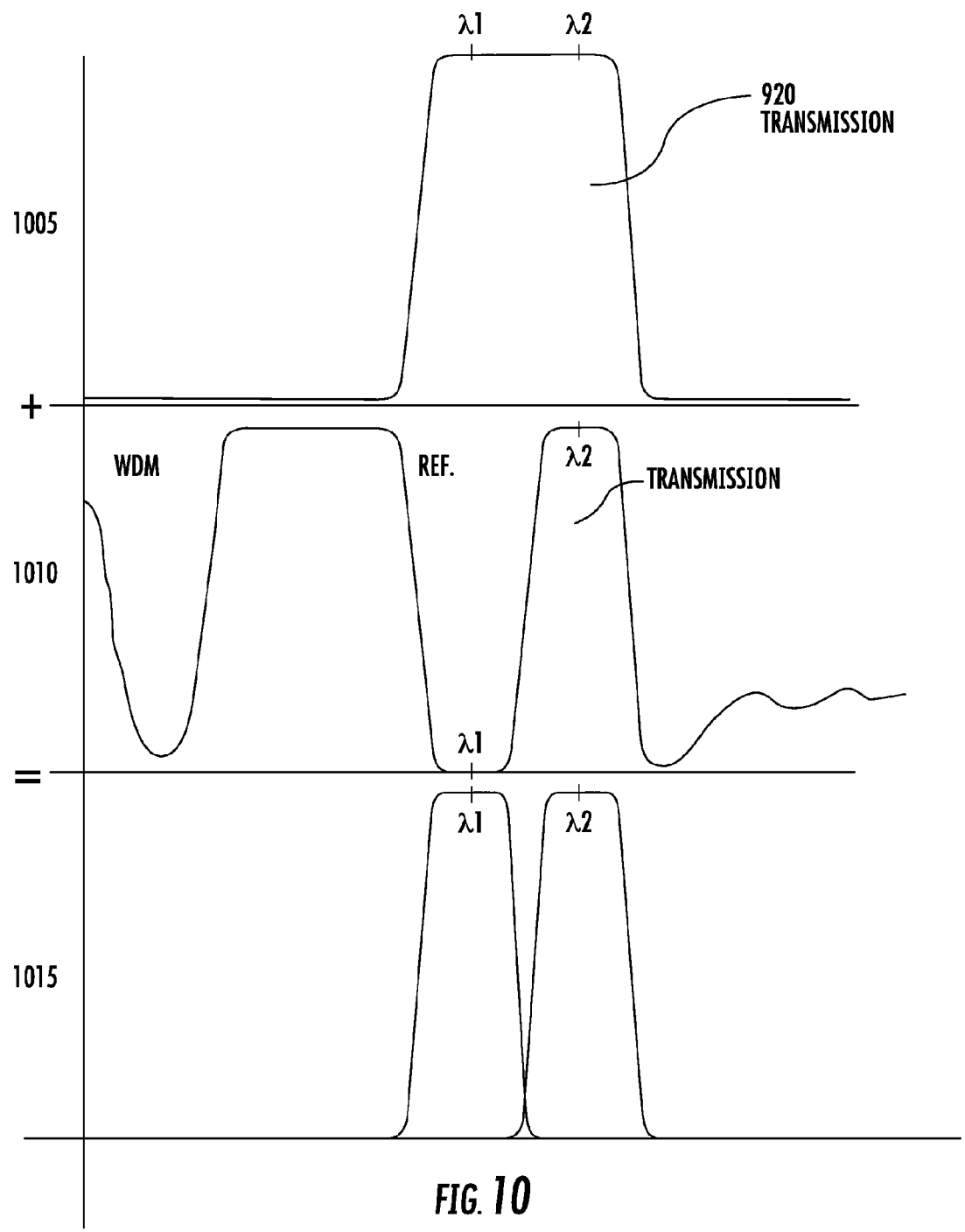
FIG. 10 shows an example spectrum in accordance with aspects of the present disclosure.

FIG. 10 shows an example spectrum (intensity versus wavelength) as modified by the WDM filter in accordance with implementations of the present teachings. At 1005, a transmission spectrum is shown having a broad peak for wavelengths $\lambda_1$ and $\lambda_2$. At 1010, a transmission is shown as modified by the WDM filter where radiation at or about $\lambda_1$ is reflected by the WDM filter and radiation at or about $\lambda_2$ is transmitted by the WDM filter. At 1015, the sum of the spectrum of 1005 and 1010 having distinct transmission peaks at or about wavelengths $\lambda_1$ and $\lambda_2$.

Figure 11:
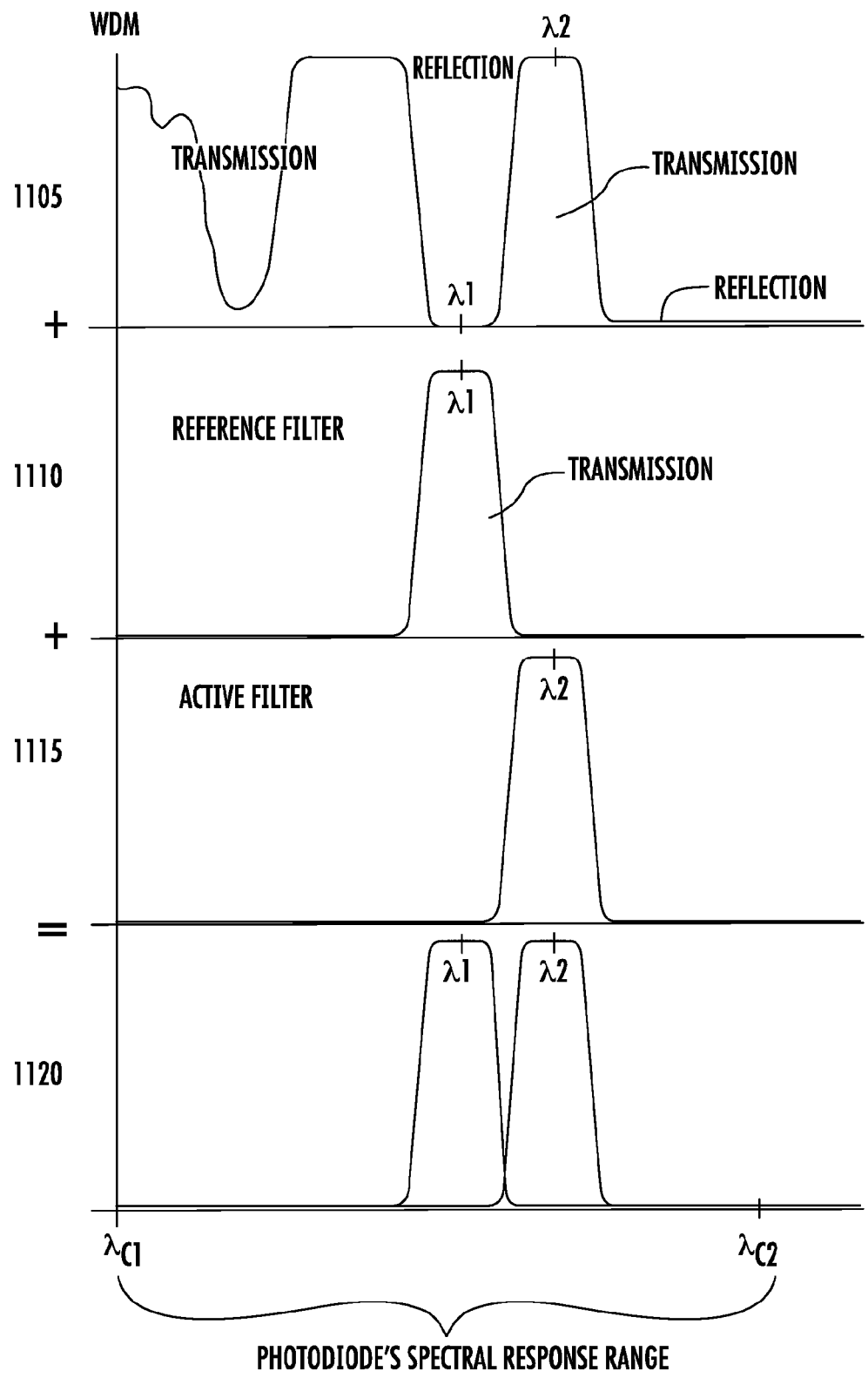
FIG. 11 shows another example spectrum in accordance with aspects of the present disclosure.

FIG. 11 shows another example spectrum (intensity versus wavelength) as modified by the WDM filter in accordance with implementations of the present teachings. The spectral response range of the photodiodes can span a range of wavelengths encompassing wavelengths $\lambda_1$ and $\lambda_2$. For example, the spectral response range can include the range between about 1.2 µm and about 2.6 µm. At 1105, a spectrum is shown having a trough at or about wavelength $\lambda_1$, for example at or about 2.125 µm, due to this portion of the radiation being reflected by the WDM filter and a peak at or about wavelength $\lambda_2$, for example at or about 2.315 µm, due to this portion of the radiation being transmitted by the WDM filter. At 1110, a spectrum is shown for the reference filter having a transmission peak at or about $\lambda_1$. At 1115, a spectrum is shown for the active filter having a transmission peak at or about $\lambda_2$. At 1120, the sum of 1105, 1110, and 1115 is shown having distinct transmission peaks at or about wavelengths $\lambda_1$ and $\lambda_2$.

Figure 12:
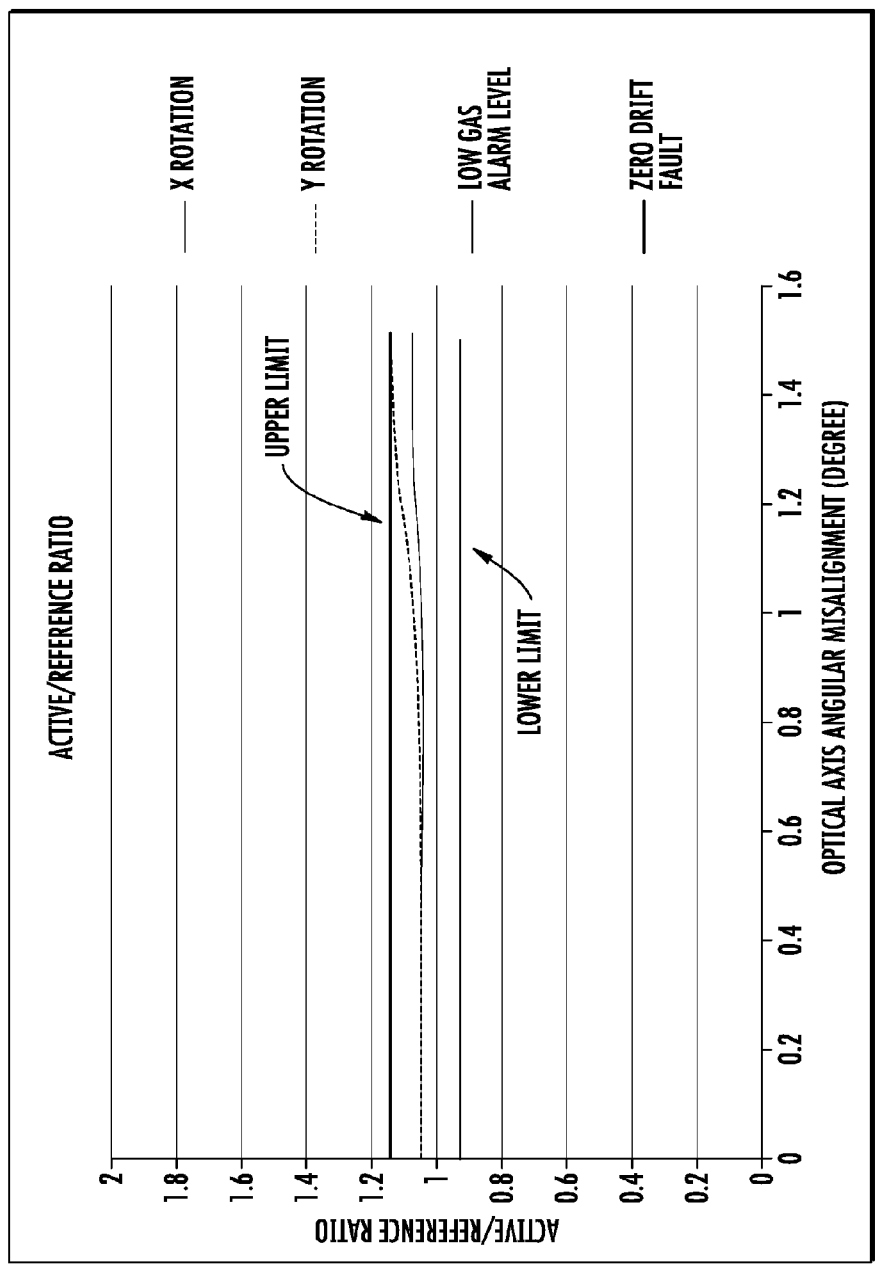
FIG. 12 shows a chart of the performance of the optical system ratio of FIGS. 2, 3 and 5 through a range of degrees of receiver-transmitter misalignment.

FIG. 12 shows a chart of the performance of the optical system of FIGS. 2, 3, 5 and 9, as the receiver optical axis during unintentional misalignment. In FIG. 12, during exposure to zero gas levels, are upper and lower ratio action threshold levels. The upper threshold level erroneously signifies "negative gas," which is usually caused by extreme misalignment or partial beam blocks. The lower threshold level signifies the erroneous presence of combustible gas. The space between the ratio thresholds indicates safe operation. As the ratio goes below the lower level, dangerous levels of gas are indicated. Imaging optical systems are prone to generate significant errors during misalignment scenarios such as high winds bending mounting poles, or passing locomotives causing local sinking of the earth, or wave action bending boat hulls in marine applications. The top-hat optical beam shape mitigates the misalignment problems.

FIG. 13 shows an irradiance map that illustrates the optical performance of an imaging and non-imaging optical system as a measure of the intensity over the angle of misalignment. The central two sharply focused peaks, 1305 and 1310, demonstrate the changes in illumination on the active and reference photodiodes as the angle of misalignment is varied in an imaging optical design. A comparable scan of non-imaging optical system with top-hat optics is shown for comparison. The light intensity is nearly uniform in both photodiodes showing the improvement in misalignment stability. In the figure, the power under both sets of curves is approximately equal.

The foregoing description is illustrative, and variations in configuration and implementation may occur to persons skilled in the art. Other resources described as singular or integrated can in implementations be plural or distributed, and resources described as multiple or distributed can in implementations be combined. The scope of the present teachings is accordingly intended to be limited only by the following claims.

What is claimed is:

1. An open path gas detector comprising:
an optical element operable to receive radiation from an objective optical element and separate the radiation into a first radiation portion and a second radiation portion;
a first beam-shaping optical element operable to receive the first radiation portion;
a first photodiode comprising a first active sensing region operable to receive the first radiation portion from the first beam-shaping optical element;
a filter operable to receive and filter the second radiation portion to produce a second filtered radiation portion;
a second beam-shaping optical element operable to receive the second filtered radiation portion; and
a second photodiode comprising a second active sensing region operable to receive the second filtered radiation portion from the second beam-shaping optical element;
wherein the first beam-shaping optical element and the second beam-shaping optical element are operable to provide a substantially uniform illumination intensity profile across an entire first active sensing region of the first photodiode and the second active sensing region of the second photodiode.

2. The open path gas detector of claim 1, wherein the optical element comprises a beam splitter.

3. The open path gas detector of claim 1, wherein the optical element comprises a wavelength-division multiplexing (WDM) filter.

4. The open path gas detector of claim 1, further comprising a reference filter operable to receive and filter the first radiation portion to produce a first filtered radiation portion to be provided to the first photodiode.

5. The open path gas detector of claim 2, wherein the beam splitter is operable to produce the first radiation portion and the second radiation portion with substantially equal intensities.

6. The open path gas detector of claim 3, wherein the WDM filter is operable to separate the radiation by wavelength.

7. The open path gas detector of claim 1, wherein any, or combinations of, the optical element, the objective optical element, the filter, the first beam-shaping optical element, and the second beam-shaping optical element comprises a reflective optical component, a refractive optical component, or both a reflective and a refractive optical component.

8. An open path gas detector comprising:
an optical element operable to receive radiation from an objective optical element and separate the radiation into a first radiation portion and a second radiation portion;
a first beam-shaping optical element operable to receive the first radiation portion;
a first photodiode comprising a first active sensing region operable to receive the first radiation portion from the first beam-shaping optical element;
a filter operable to receive and filter the second radiation portion to produce a second filtered radiation portion;
a second beam-shaping optical element operable to receive the second filtered radiation portion;
a second photodiode comprising a second active sensing region operable to receive the second filtered radiation portion from the second beam-shaping optical element;
a reference field stop positioned near a focal point of the first radiation portion between the optical element and the first beam-shaping optical element; and
an active field stop positioned near a focal point of the second radiation portion between the optical element and the second beam-shaping optical element.

9. The open path gas detector of claim 8, wherein the reference field stop comprises an aperture with a diameter smaller than an aperture of the active field stop.

10. The open path gas detector of claim 9, where in the aperture of the active field stop and the aperture of the reference field stop are adjustable to compensate for changes in alignment of the radiation received by the optical element.

11. The open path gas detector of claim 1, wherein the first beam-shaping optical element and the second beam shaping optical comprises any, or combinations of, one or more Kohler lenses, one or more Fly's Eye lenses, one or more Micro-lens arrays, one or more Micro-lens beam homogenizer, one or more faceted tubes, one or more compound parabolic lenses, and combinations thereof.

12. An open path gas detector comprising:
an optical element operable to receive radiation;
a wavelength-division multiplexing (WDM) filter operable to receive the radiation from the optical element and separate the radiation into a first wavelength portion and a second wavelength portion;
a first photodiode comprising a first active sensing region operable to receive the first wavelength portion;
a filter operable to receive and filter the second wavelength portion to produce a second filtered wavelength portion; and
a second photodiode comprising a second active sensing region operable to receive the second filtered wavelength portion from the second filter;
wherein the radiation provided to the first active sensing region of the first photodiode and the second active sensing region of the second photodiode comprises a substantially uniform illumination intensity profile across an entire first active sensing region of the first photodiode and the second active sensing region of the second photodiode.

13. The open path gas detector of claim 12, wherein the objective optical element comprises a reflective optical component, a refractive optical component, or both a reflective and a refractive optical component.

14. The open path gas detector of claim 12, further comprising a reference filter operable to receive and filter the first wavelength portion to produce a first filtered wavelength portion to be provided to the first photodiode.

15. An open path gas detector comprising:
an optical element operable to receive radiation;
a wavelength-division multiplexing (WDM) filter operable to receive the radiation from the optical element and separate the radiation into a first wavelength portion and a second wavelength portion;
a first photodiode comprising a first active sensing region operable to receive the first wavelength portion;
a filter operable to receive and filter the second wavelength portion to produce a second filtered wavelength portion;
a second photodiode comprising a second active sensing region operable to receive the second filtered wavelength portion from the second filter;
a reference field stop positioned near a focal point of the first radiation portion between the optical element and a first beam-shaping optical element; and
an active field stop positioned near a focal point of the second radiation portion between the optical element and a second first beam-shaping optical element.

16. The open path gas detector of claim 15, wherein the reference field stop comprises an aperture with a diameter smaller than an aperture of the active field stop.

17. The open path gas detector of claim 16, where in the aperture of the active field stop and the aperture of the reference field stop are adjustable to compensate for changes in alignment of the radiation received by the optical element.

18. The open path gas detector of claim 15, wherein the first beam-shaping optical element and the second beam-shaping optical element are operable to provide a substantially uniform illumination intensity profile across an entire portion of the first active sensing region of the first photodiode and the second active sensing region of the second photodiode.

19. The open path gas detector of claim 12, wherein the detector comprises a field of view of sufficient size to allow for transmitter-to-receiver misalignments.

20. The open path gas detector of claim 12, wherein additional WDM filters are configured to allow multiple channels at different wavelengths to detect multiple gases.

21. The open path gas detector of claim 15 wherein the first beam-shaping optical element comprises a Kohler lens.

* * * * *